United States Patent
Mirvakili et al.

(12)

(10) Patent No.: US 11,065,101 B2
(45) Date of Patent: Jul. 20, 2021

(54) FAST TORSIONAL ARTIFICIAL MUSCLES FROM TWISTED YARNS OF SHAPE MEMORY MATERIAL

(71) Applicant: Massachusetts Institute of Technology, Cambridge, MA (US)

(72) Inventors: Seyed M. Mirvakili, Vancouver (CA); Ian W. Hunter, Lincoln, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 16/483,881

(22) PCT Filed: Mar. 13, 2018

(86) PCT No.: PCT/US2018/022087
§ 371 (c)(1),
(2) Date: Aug. 6, 2019

(87) PCT Pub. No.: WO2018/182964
PCT Pub. Date: Oct. 4, 2018

(65) Prior Publication Data
US 2020/0022803 A1    Jan. 23, 2020

Related U.S. Application Data

(60) Provisional application No. 62/477,008, filed on Mar. 27, 2017.

(51) Int. Cl.
*F03G 7/06* (2006.01)
*A61F 2/08* (2006.01)
(Continued)

(52) U.S. Cl.
CPC .............. *A61F 2/08* (2013.01); *D02G 3/02* (2013.01); *D02G 3/26* (2013.01); *D02J 13/001* (2013.01);
(Continued)

(58) Field of Classification Search
None
See application file for complete search history.

(56) References Cited

U.S. PATENT DOCUMENTS 6,410,886 B1 *  6/2002  Julien ............... H05B 3/12
                                                148/245
10,174,745 B2 *  1/2019  Gurley ............... F03G 7/065
(Continued)

OTHER PUBLICATIONS

Mirvakili, Seyed M., "High performance materials for artificial muscles and energy storage devices"; Massachusetts Institute of Technology Libraries, Cambridge, MA; Jun. 21, 2017; 148 pp.
(Continued)

*Primary Examiner* — George Wyszomierski
(74) *Attorney, Agent, or Firm* — Sunstein LLP

(57) ABSTRACT

A torsional actuator formed of a yarn of twisted shape memory material. The yarn has multiple strands of homogeneous shape memory material that have been homochirally twisted. For torsional actuation, a fractional portion of the yarn is heated such as by Joule heating. Various Joule heating mechanisms include passing an electrical current through an unwound segment of the yarn, or by coating a fractional portion of the length of each homogeneous strand with a coating material of higher electrical conductivity than the electrical conductivity of the shape memory material an passing current through the length of the yarn. The shape memory material may be a shape memory alloy such as a NiTi alloy.

6 Claims, 10 Drawing Sheets

(51) Int. Cl.
 *D02G 3/02* (2006.01)
 *D02G 3/26* (2006.01)
 *D02J 13/00* (2006.01)

(52) U.S. Cl.
 CPC ...... *F03G 7/065* (2013.01); *A61F 2002/0894* (2013.01); *D10B 2101/20* (2013.01)

(56) References Cited

U.S. PATENT DOCUMENTS

| | | | |
|---|---|---|---|
| 10,407,939 B2* | 9/2019 | Lacarbonara | F03G 7/065 |
| 2005/0150223 A1* | 7/2005 | Rey | F03G 7/065 |
| | | | 60/527 |
| 2009/0226691 A1* | 9/2009 | Mankame | D07B 1/0673 |
| | | | 428/222 |
| 2015/0219078 A1 | 8/2015 | Li et al. | |

OTHER PUBLICATIONS

Mirvakili et al., "A torsional artificial muscle from twisted nitinol microwire", Abstract, Proceedings SPIE, vol. 10163, Electroactive Polymer Actuators and Devices (EAPAD) Apr. 17, 2017; 9 pp.

Mirvakili et al., "Fast Torsional Artificial Muscles from NiTi Twisted Yarns", Abstract, ACS Applied Materials and Interfaces; vol. 9, No. 19; Apr. 27, 2017; 6 pp.

Paik et al., "A novel low-profile shape memory alloy torsional actuator", Smart Materials and Structures; vol. 19, No. 125014; Nov. 17, 2010; pp. 1-9.

Kianzad, "A treatise on highly twisted artificial muscle: thermally driven shape memory alloy and coiled nylon actuators", University of British Columbia, Oct. 24, 2015; 99 pp.

Cherubini et al., "Experimental characterization of thermally-activated artificial muscles based on coiled nylon fishing lines", AIP Advances, vol. 5, No. 067158, Jun. 2015; pp. 1-11.

ISA/US, International Searching Report and Written Opinion, International Application No. PCT/US18/22087, dated Jun. 5, 2018; 24 pp.

* cited by examiner

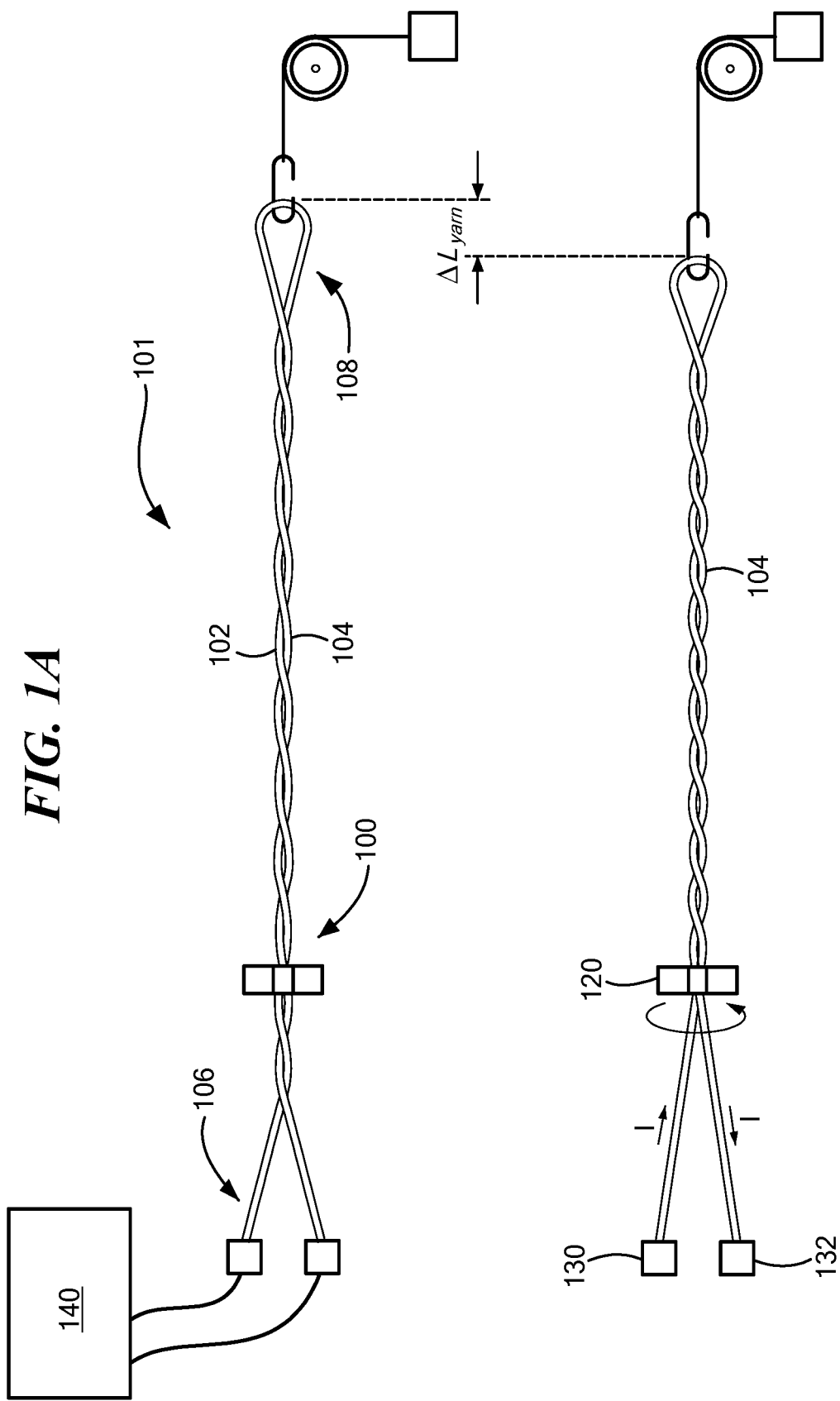

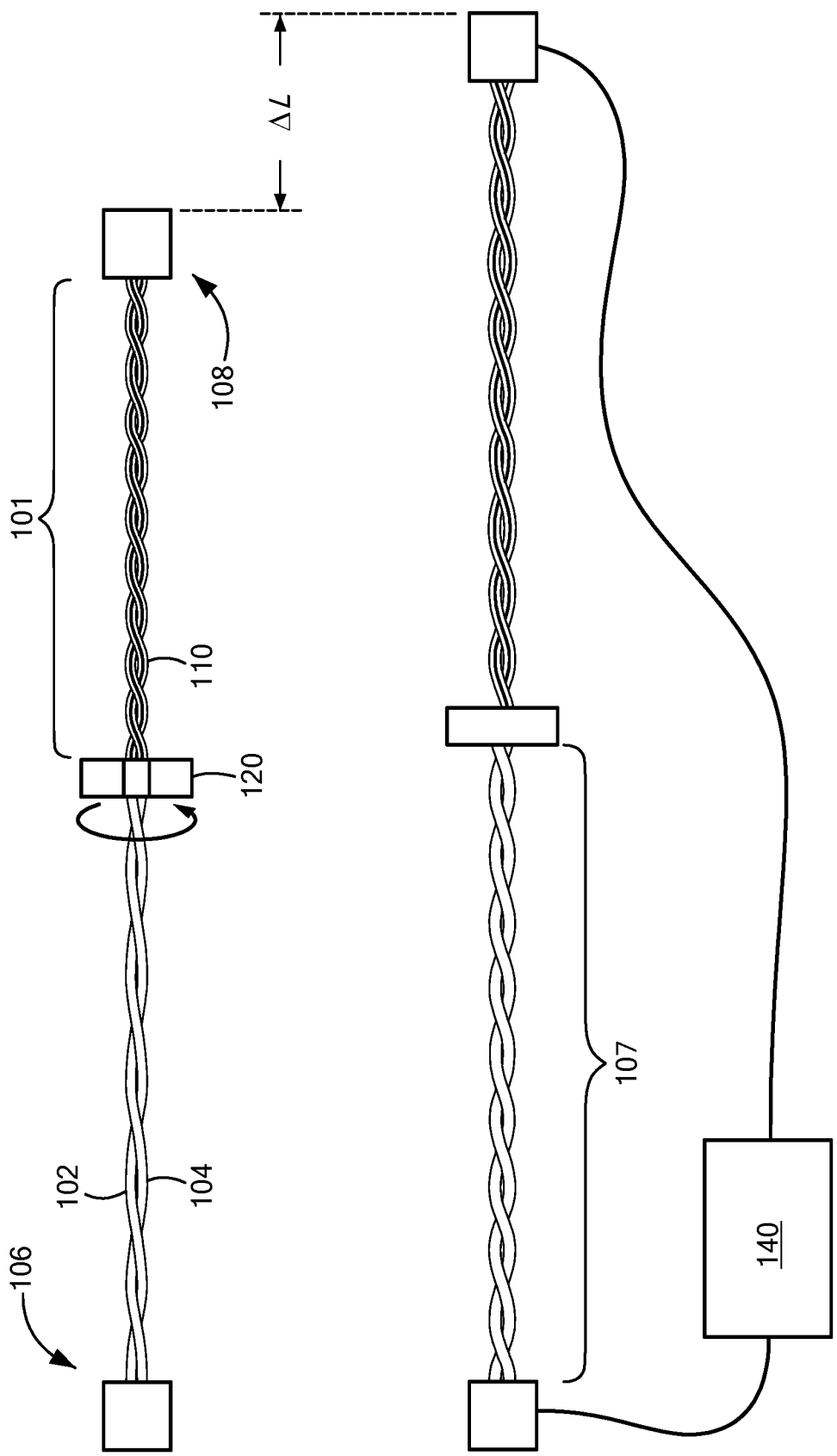

FAST TORSIONAL ARTIFICIAL MUSCLES FROM TWISTED YARNS OF SHAPE MEMORY MATERIAL

CROSS-REFERENCE TO RELATED APPLICATIONS

This application is the national phase entry of International Patent Application No. PCT/US2018/022087 filed Mar. 13, 2018, which claims the priority of U.S. Provisional Application No. 62/477,008, filed Mar. 27, 2017, the disclosures of which are hereby incorporated by reference in their entirety.

TECHNICAL FIELD

The present invention relates to torsional actuators and methods for manufacturing and using them, and, more particularly, to thermally activated torsional actuators of shape memory materials such as shape memory alloys.

BACKGROUND ART

Artificial muscles are materials or devices that can reversibly contract, expand, or rotate within a single integral structure due to an external stimulus (such as voltage, current, pressure or temperature). Performance metrics of artificial muscles include cycle life, gravimetric/volumetric energy and/or power density, efficiency, cost, and controllability.

Enhancing such performance characteristics of artificial muscles has been an active field of research and has encompassed such materials as conducting polymers, dielectric elastomers, carbon nanotubes and graphene, to list a number of examples.

An early flexible pneumatic actuator led to the development of the "Heidelberg Hand," by Dr. O. Häfner at the Orthopaedic Hospital in Heidelberg in 1948, and the McKibben artificial muscle. Initial application of artificial muscles to various orthotic appliances spurred a succession of new artificial muscle designs. A current review of research in the field of artificial muscles may be found in Mirakili et al., "*Artificial Muscles: Mechanisms, Applications, and Challenges,*" *Adv. Mater.*, vol. 2018, 1704407, (Dec. 18, 2017, hereinafter, "Mirvakili, 2018"), which, for convenience, is incorporated herein by reference, but which is not prior art to the present application.

One class of artificial muscle, torsional actuators, provides for application of a torque to one mechanical member with respect to another mechanical member. For example, pneumatic torsional artificial muscles are one of the derivatives of the McKibben artificial muscle where, instead of having a double family of fibers braided around a bladder, a single family of fibers may be used. Asymmetric braiding translates volumetric expansion in a bladder into a torsional actuation and unwinding of inextensible fibers.

Definitions: As the term is used herein, the term "strand" is used to refer to any object of a generally cylindrical shape whose length dimension exceeds any transverse dimension by at least two orders of magnitude. Thus, for current purposes, a wire, regardless of composition, is a "strand." A strand may also be referred to herein as a "filament." A substantially linear member having only a single strand may be referred to herein as a "monofilament."

The term "yarn" shall refer to a length of twisted strands. Yarns are "two-ply" if they have two twisted strands, and "multi-ply" or "N-ply" if they have any number of strands exceeding one.

Multiple strands are said to be "homogeneous" if their compositions are identical and "heterogeneous" if they are not.

Strands of a yarn are "homochirally" twisted when all strands share the same chiral sense.

Twisted yarns of multi-walled carbon nanotubes (MWCNT) or niobium nanowires can produce a torsional actuation in response to heat when half of the length of the yarn is infiltrated with a stimulus-responsive guest material such as wax, as described, for example, by Lima et al., "*Electrically, Chemically, and Photonically Powered Torsional and Tensile Actuation of Hybrid Carbon Nanotube Yarn Muscles,*" *Science*, vol. 338, pp. 928-32, (2012) (hereinafter, "Lima, 2012"), incorporated herein by reference. Lima, 2012 demonstrated that MWCNT twisted yarns have shown rotational speeds of up to 11,500 revolutions per minute and a remarkable gravimetric torque of 8 N·m/kg, higher than that of ungeared commercial direct drive electric motors (2-6 N·m/kg).

Operation of a novel torsional actuator, employing a physical mechanism entirely distinct from that of the MWCNT twisted yarns, is the subject of the present invention, described in detail below.

Gabriel et al., "A micro rotary actuator using shape memory alloys," *Sens. Actuators*, vol. 15, pp. 95-102, (1988) (hereinafter, "Gabriel, 1988"), incorporated herein by reference, employed differential heating of a single rod of shape memory alloy for torsional actuation. Wires of shape memory alloy (SMA) (defined below, and including, for example, NiTi) have been used in a variety of actuators, for example, as described in Hunter, et al., in "*Fast reversible NiTi fibers for use in microrobotics,*" in *Proc. IEEE Micro Electro Mechanical Systems*, 1991, pp. 166-170 (1991), incorporated herein by reference. The use of SMAs in rotary actuator designs has been described by Gabriel, 1988, and, additionally, in:

Hwang et al., "*A Rotary Actuator Using Shape Memory Alloy (SMA) Wires,*" *IEEE ASME Trans. Mechatron.*, vol. 19, pp. 1625-35, (2014); and Rodrigue et al., "A shape memory alloy-based soft morphing actuator capable of pure twisting motion," *J. Intell. Mater. Syst. Struct.*, vol. 26, pp. 1071-78, (2015);

all three of which publications (Gabriel, Hwang and Rodrigue) are incorporated herein by reference. Gabriel, 1988, for example, demonstrated that by twisting a single 100-µm-diameter NiTi wire and differentially heating it along its length, the wire retains its programmed shape (i.e., the shape of straight wire with no twists) and produced reversible torsional actuation. However, the torsional stroke was limited to only 0.6° per millimeter of wire and required having a third electrical contact to the middle of the wire, thereby possibly reducing its range of applications.

All prior art rotation actuators that have been based on the twisting of a filament have either been monofilamentary or heterogeneous in composition, requiring, for example, conductive yarns with wax.

SUMMARY OF EMBODIMENTS OF THE INVENTION

Definition: As used herein and in any appended claims, the term "shape memory material" shall encompass any material that, upon heating above a heating transition temperature, returns to an original shape. That heating transition temperature associated with a specified shape memory material shall be referred to herein as the "activation temperature" associated with the specified shape memory material, or as the "transition temperature." Shape memory materials may include shape memory alloy fibers, such as nickel-titanium or copper-aluminum-nickel, or other alloys of zinc, copper, gold and iron, for example, or certain polymers, or any material containing the foregoing as part of its composition. Any of these materials fall within the scope of the invention described and claimed herein.

In accordance with embodiments of the invention, a novel torsional actuator is provided. The torsional actuator has a yarn that includes a homochirally twisted plurality of homogeneous strands of shape memory material and a controller for programmable heating of at least a portion of the yarn.

In accordance with other embodiments of the present invention, the programmable heating may include Joule heating. The Joule heating includes electrical current flow traversing the entire yarn. A fractional portion of the length of each homogeneous strand may be coated with a coating material of higher electrical conductivity than the electrical conductivity of the shape memory material.

In further embodiments of the present invention, the homochirally twisted plurality of homogeneous strands may include at least two strands of shape memory alloy, such as an alloy that contains nickel and titanium. The shape memory material may be nitinol microwire.

In accordance with another aspect of the present invention, a method is provided for torsional actuation that includes differentially heating portions of a twisted yarn comprising homochirally twisted homogeneous shape memory material. The differential heating of portions of the twisted yarn may be by Joule heating. Joule heating may be applied, more particularly, by directing electrical current through a portion of the yarn. In other embodiments, differential heating may be applied, alternatively, inductively, conductively, or radiatively.

In further embodiments of the invention, the shape memory material may be a NiTi alloy, such as nitinol microwire.

BRIEF DESCRIPTION OF THE DRAWINGS

The foregoing features of the invention will be more readily understood by reference to the following detailed description, taken with reference to the accompanying drawings, in which:

FIG. 1A depicts a yarn formed of twisted strands of SMA, in accordance with one embodiment of the present invention; FIG. 1B depicts the embodiment of FIG. 1A with current applied at one end of a yarn to provide Joule heating of the yarn;

FIG. 1C depicts a yarn formed of twisted strands of SMA, in accordance with another embodiment of the present invention in which a portion of the yarn is coated with gold or another electrically conductive material; FIG. 1D depicts the embodiment of FIG. 1A with current applied from end to end of a yarn to provide Joule heating of the yarn;

In FIG. 3A, the pulse width is smaller than the time it takes for the yarn to reach the maximum torsional stroke, while in FIG. 3B, the pulse width is longer. In FIG. 3C, linear actuation of a twisted pair torsional actuator excited with a 500 ms voltage pulse is plotted.

DETAILED DESCRIPTION OF EMBODIMENTS OF THE INVENTION

Figure 1E:
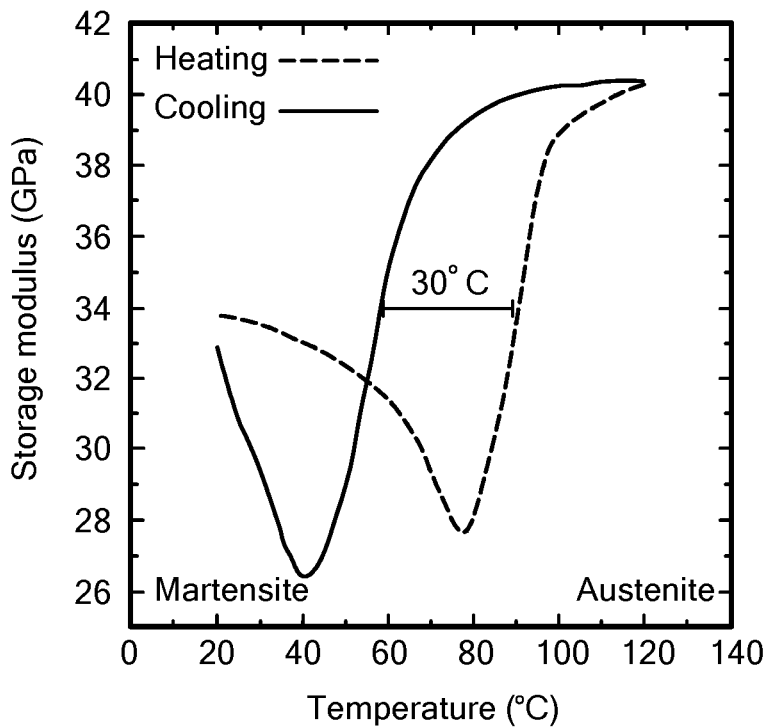
FIGS. 1E and 1F plot, respectively, measured storage modulus $\varepsilon'$ and phase lag $\delta$ between stress and strain in an SMA as functions of temperature.

Definitions: Unless otherwise specified or required by context, terms used herein shall have the following meanings:

Output Strain ($\varepsilon$): The change in length upon excitation normalized to the initial length.

Output Stress ($\sigma$): The generated force upon excitation normalized to the initial cross-sectional area of the muscle at rest (engineering stress, $\sigma_E$) or at the excited state (true stress, $\sigma_T$).

Cycle Life: The number of cycles an artificial muscle can survive before failure.

The term storage modulus $\varepsilon'$ refers to the elastic portion of the ratio of stress to strain in a material.

The word "fractional" is defined to mean assuming a real value greater than 0 and less than 1.

"Joule heating," or, synonymously, "Ohmic heating," refers to heating of a material having finite electrical resistivity by passage therethrough of an electrical current.

As described in detail herein, twisted two-ply (or multi-ply) yarns of fine NiTi fibers are applied, employing a never-suggested working mechanism to achieve torsional activation. One of the major advantages of homogeneous NiTi fibers (all strands made of the same material) over CNTs or nanowire yarns is that they do not need any guest material for actuation and are commercially available which makes them suitable for immediate applications. For example, since no guest materials such paraffin wax or rubber is needed, a torsional actuator in accordance with the present invention may advantageously be used in vacuum.

In the present work, it is shown that, by twisting multiple strands of NiTi wires in a yarn and applying heat to a portion of the yarn's length, a reversible torsional and linear actuation may be attained. The required heat may be generated, for example, by Joule heating of the NiTi fibers. It is to be understood, however, that other mechanisms for heating a portion of the yarn are encompassed within the scope of the present invention. Thus, for example, a portion of the yarn may be heated radiatively or conductively, or by inducing a current in a portion of the yarn. To confine the Joule heating to only half (or other fractional portion) of the yarn's length, resistance of the other complementary portion may be lowered by a factor of 15-20 by electroplating a thin layer of gold on the fibers. One exemplary NiTi alloy wire has an electrical resistivity of 0.8 μΩ·m and 1 μΩ·m in its Martensite and Austenite phases respectively. Since the gold coating has a much higher electrical conductivity than that of the NiTi fiber, the gold coating carries almost all the current. Therefore, almost no gold-coated NiTi fiber reaches the activation temperature when the voltage is applied.

Certain embodiments of the present invention are now described with reference to FIGS. 1A and 1B. A yarn, designated generally by numeral 100, is formed by twisting two strands (or "fibers") 102, 104 of a shape memory material. Strands 102, 104 of SMA may be formed of a single looped length of shape memory material, as shown, however they may also be separate lengths. In certain embodiments of the present invention, yarn 100 is constrained to prevent rotation at either of ends 106 and 108. In the embodiment of FIGS. 1A and 1B, a programmed electrical potential is applied by controller 140 across ports 130 and 132 as a function of time to supply a current 134 through the shape memory material to cause Joule heating of the untwisted end 106 of the yarn 100. More generally, controller 140 provides programmable differential heating of portions of yarn 100, whether by supplying current as described in the foregoing example, or otherwise.

Another embodiment of the present invention is now described with reference to FIGS. 1C and 1D. Yarn 100 is again formed by twisting two strands (or "fibers") 102, 104 of a shape memory material. In certain embodiments of the present invention, yarn 100 may be constrained to prevent rotation at either of ends 106 and 108. A portion 101 of yarn 100 is coated with a thin layer 110 of a material, such as gold, characterized by an electrical conductivity exceeding that of the shape memory material by at least two orders of magnitude. The uncoated portion of yarn 100 is referred to herein as "bare" portion 107. In the embodiment of FIGS. 1C and 1D, a current supplied by controller 140 flows through the entire length of yarn 100.

It is to be understood that, while the invention is described in terms of Joule heating, all other means of differential heating are within the scope of the claimed invention. Thus, for example, heating may be achieved radiatively or inductively by differential absorption of electromagnetic radiation by respective portions of the yarn.

The shape memory material may be an SMA such as NiTi, and, in fact, the invention is described herein in terms of NiTi for purposes of heuristic convenience. However, the scope of the present invention encompasses all other shape memory materials used in this manner that are known or that may be discovered in the future.

A method by which yarn 100 may be prepared is by homochirally twisting NiTi wires (each 25 μm in diameter) with a transition temperature of 90° C. (available from Dynalloy Inc. of Irvine, Calif.). Gold plating solution may be used to gold-coat a fractional length of NiTi yarn 100, however other techniques for coating the yarn are within the scope of the present invention.

A profound physical difference between the working principle of the shape memory material torsional actuator of the present invention and any torsional actuator based on wax-infiltrated yarns (such as yarns infiltrated with paraffin) is that, in wax-infiltrated yarns, upon Joule heating, the volume of the wax expands (by almost 30%, in the case of paraffin wax) during the solid to liquid phase transition process. Since the wax-infiltrated yarn is prevented from rotation at both ends (in a manner analogous to the embodiment of the present invention depicted in FIG. 1A) and since each individual fiber of a wax-infiltrated yarn is inextensible, the expansion in volume of the wax-infiltrated part leads to an untwist in that part and a twist in the bare part.

In contrast to operation of a wax-infiltrated yarn, each fiber 102, 104 of an SMA twisted yarn 100 in accordance with the present invention untwists to recover its initial form therefore, the gold coated part 101 twists and stores energy, as depicted in FIG. 1C. This energy is then released to restore the twisted yarn 100 to its initial state during the turn off cycle. To better observe this behavior, a paddle 120, made of a piece of aluminum sheet, for example, may be attached to the middle of the yarn 100 at the boundary of the gold-coated part 101 and the bare section 106 of the yarn.

Figure 1F:
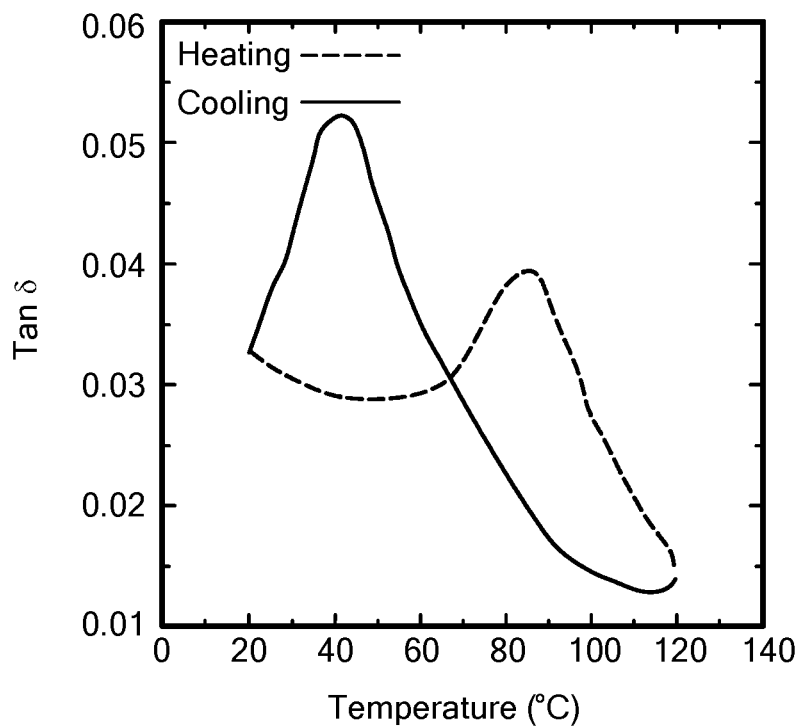

Dynamic mechanical behavior of NiTi and other shape memory alloys has been well-studied, and discussed, for example in Vitiello et al., "*Analysis of thermomechanical behaviour of Nitinol wires with high strain rates,*" *Smart Mater. Struct.*, vol. 14, pp. 215-21, 2005, incorporated herein by reference. Results of measurements performed using a dynamic mechanical analyzer (DMA) on a piece of 25-μm NiTi alloy wire are shown in FIGS. 1E and 1F. FIG. 1E depicts an increase in storage modulus ε' by almost 18% during the phase transition from Martensite to Austenite phases. Changes with temperature are shown for heating and cooling phases respectively. The behavior of oriented nylon fibers (used in nylon artificial muscles) is in sharp contrast to that of SMAs, in that the storage modulus of oriented nylon fibers decreases by almost 88% over a similar temperature range. The increase in storage modulus ε' positively affects the generated torque in that it modifies the torsional spring constant, and reversibility of the torsional stroke. FIG. 1F plots the measured phase lag δ between stress and strain in an SMA as a function of temperature for heating and cooling cycles, respectively.

To illustrate the working mechanism of the torsional actuation in NiTi fibers, the behavior of a twisted yarn consisting of only two NiTi fibers (each 25 μm in diameter) and a larger number N of fibers is discussed, and performance scalability evaluated.

The torsional actuation mechanism in NiTi twisted yarns is based on two phenomena: (1) shape recovery of the twisted NiTi individual microwires upon excitation and (2) contraction and expansion in the length and the diameter of the individual microwires, respectively. Upon twisting of the yarn in the fabrication process which is analogous to 2-, 4-, or 6-ply homochiral nanofiber twisted yarns, aside from the fiber bundle, each individual NiTi microwire twists as well. In the shape recovery stage, each individual strand untwists to recover its original shape which also causes the bundle to untwist. The twisted NiTi microwires can be seen as intertwined helices with a coil index of 1 (where the coil index refers to the ratio of mean coil diameter to the fiber diameter). Therefore, we can explain the actuation mechanism from the spring mechanics. From the equations of torsion and curvature, we can find the torsional stroke (ΔN/N) to be:

$$\frac{\Delta N}{N} = 3\frac{\Delta L}{L} - \frac{\Delta h}{h} - \frac{1}{2}\frac{\Delta d}{d} + \frac{\Delta n}{n}. \qquad \text{Equation 1}$$

where N is the number of turns in the coil, L is the length of individual fibers, h is the length of the active section of the twisted yarn, d is the diameter, which is measured from the center of the fibers, n is the number of inserted twists, and Δn is the change in the inserted twists of the microwire during the shape recovery process. For a one-end-tethered yarn, the individual microwires can recover their initial shape in the absence of a counterbalancing torque. Therefore, all the twists in each individual microwire will be translated to the paddle (assuming friction is negligible). However, for a two-end-tethered yarn, since one-half of the yarn is acting as a bias spring, the fibers in the bare part cannot completely recover their initial shape; therefore, only a fraction of the twist in individual microwires rotate the paddle.

As illustrated in FIG. 1C, on activation, the bare part of the yarn, strand 104, has a negative change in length ($\Delta h$) because of the activation of the NiTi fibers ($\Delta L$). The gold coated part also has a negative $\Delta h$ because of the inserted twists in the yarn and the fact that the change in length of each coated NiTi fiber is negligible.

Figure 2A:
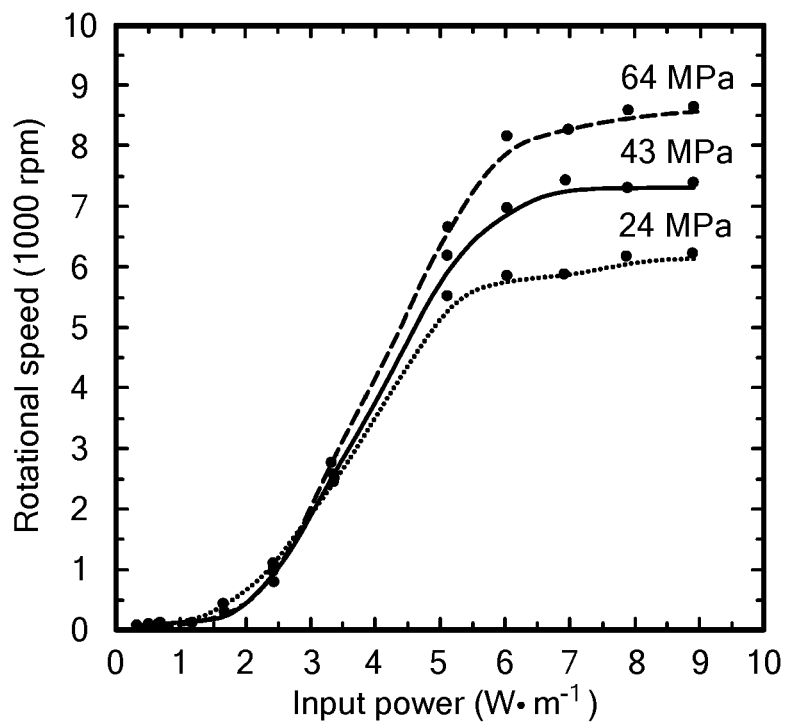
FIG. 2A plots rotational speed as a function of input power (normalized per length of the yarn) and load for a twisted-pair of NiTi fibers, in accordance with embodiments of the present invention.
Figure 2B:
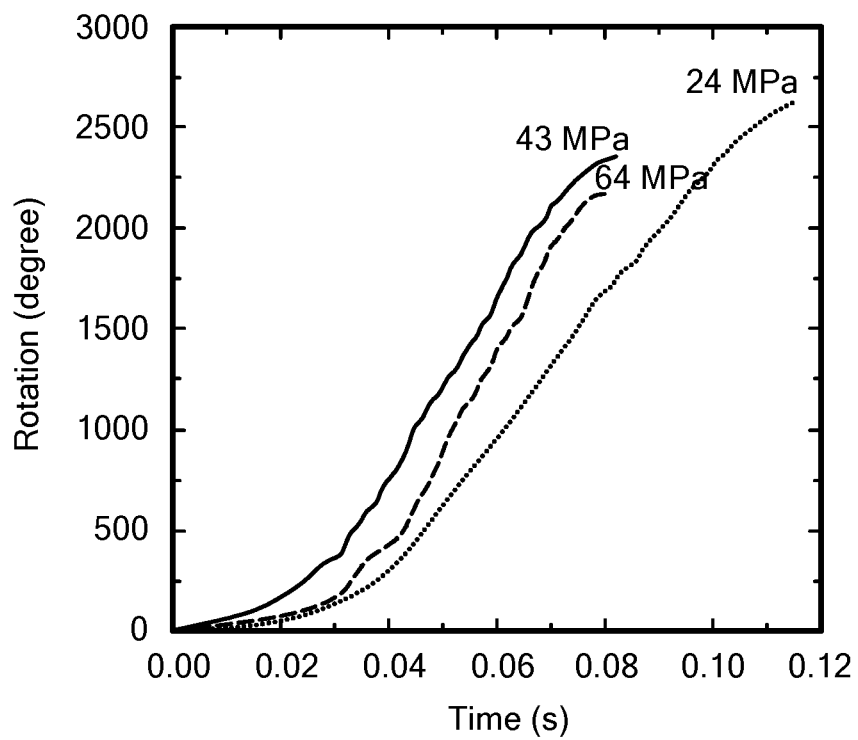
FIG. 2B plots the torsional stroke of the same yarn, while FIG. 2C provides plots of torsional stroke and rotational speed of the yarn as a function of load.
Figure 2C:
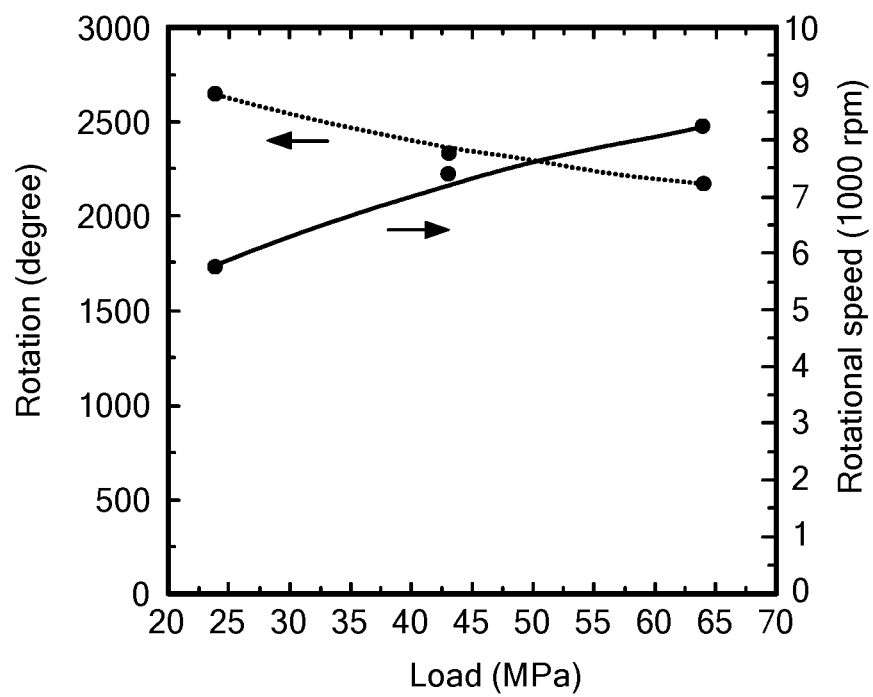

Since the contractile strain of the NiTi wires is a function of applied stress, by increasing the load size one might expect to see a larger $\Delta L$, and, since $\alpha$ is relatively small (<20°) in the samples considered, a larger $\Delta n$ might be expected. However, in fact, experimental results, now described with reference to FIGS. 2A-2C indicate that as the load is increased the torsional stroke decreases. FIG. 2A plots rotational speed as a function of input power and load for a twisted pair of NiTi fibers, in accordance with an embodiment of the present invention, with an inserted twist of 375 turns/m. Curves corresponding to loads of 24, 43 and 64 MPa are shown. FIG. 2B plots the torsional stroke of the same yarn during excitation with an input power of 875 mW. FIG. 2C provides plots of torsional stroke 220 and rotational speed 222 of the yarn as a function of load for the same yarn. For lower excitation voltages to ensure that the yarn is reaching steady state actuation, a square wave pulse at 0.5 Hz was employed. For higher voltages, faster actuation may be employed. For experimental purposes, a duty cycle of 50% was employed, however, any duty cycle is encompassed within the scope of the present invention.

The decrease in torsional stroke with increasing load can be explained by the fact that the applied stress on the yarn works against the shape recovery process by tensioning the yarn. In contrast, the rotational speed has a direct correlation with the load size, as evident in FIGS. 2A and 2C. A possible explanation for the correlation is that the shape recovery process (dominant in small loads) takes longer time to untwist the yarn to the net zero torque point (i.e., the angular position at which the torque generated by the NiTi fibers is equal to the torque exerted by the passive section of the yarn) compared with the second torsional actuation mechanism described above.

In examples studied in accordance with the teachings of the present invention, a fully reversible torsional stroke of 16°/mm and a rotational speed of up to 10,500 rpm were achieved. By applying square shape voltage pulses of 500 ms long, a 1.1% tensile actuation was achieved for a twisted pair torsional actuator under a load of 64 MPa.

Figure 3A:
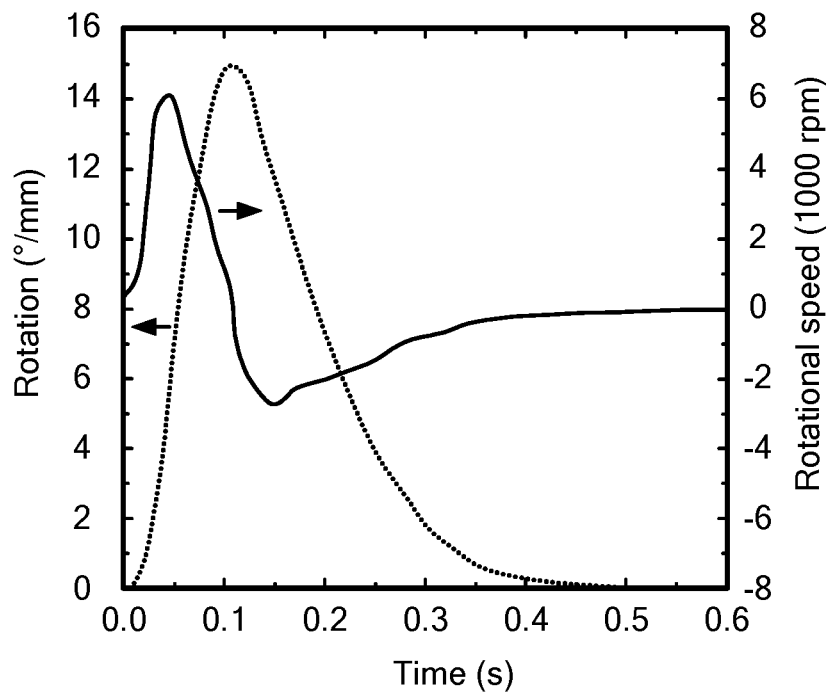
FIGS. 3A-3C plot the torsional stroke of a torsional actuator in accordance with an embodiment of the present invention.
Figure 3B:
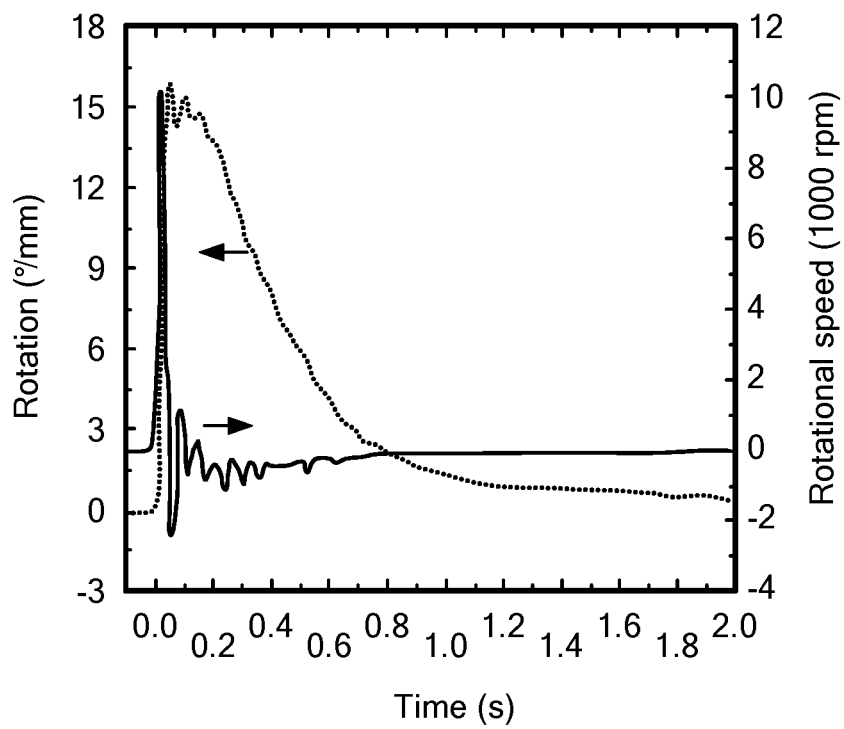

The maximum generated torque ($\tau$) by the NiTi twisted yarns can be estimated from the maximum torsional stroke ($\theta_m$) and the torsional spring constant of the yarn ($\kappa$). The torsional spring constant ($\kappa = I\omega_n^2$) can be evaluated from the moment of inertia $$\left(I = \frac{m(l^2 + w^2)}{12}\right)$$

of the paddle 120 and the natural resonance frequency $\omega_n$ of the yarn 100 which can be estimated from oscillation of the yarn observed at the net zero torque point evident in FIG. 3B.

Figure 3C:
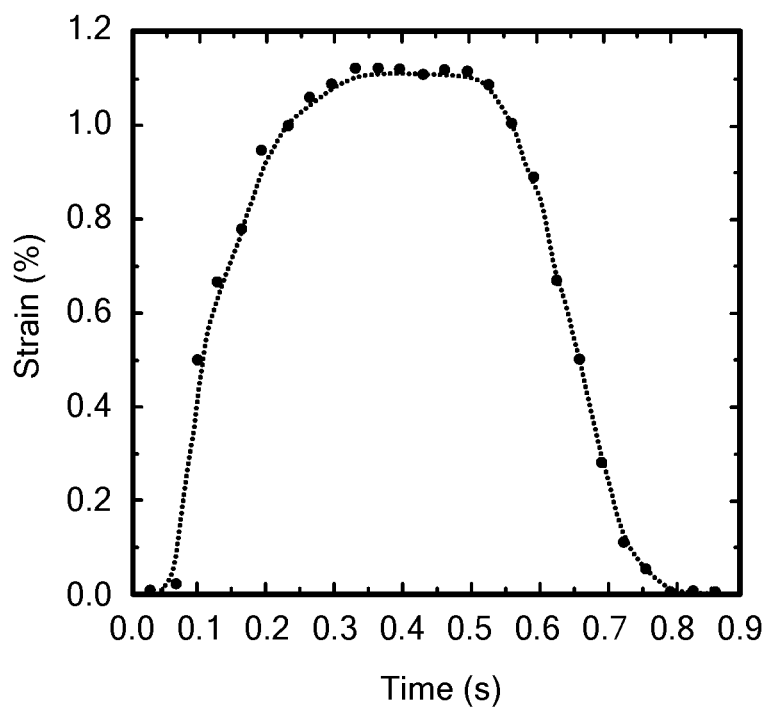

The torsional stroke of a twisted pair with 827 turns/m, excited with an 83-ms voltage pulse of 16 V, is discussed with reference to FIGS. 3A-3C. In FIG. 3A, the pulse width is smaller than the time it takes for the yarn to reach the maximum torsional stroke, while in FIG. 3B, the pulse width is longer and therefore, ringing occurs. Linear actuation of a twisted pair torsional actuator excited with a 500 ms voltage pulse is plotted in FIG. 3C.

Figure 4A:
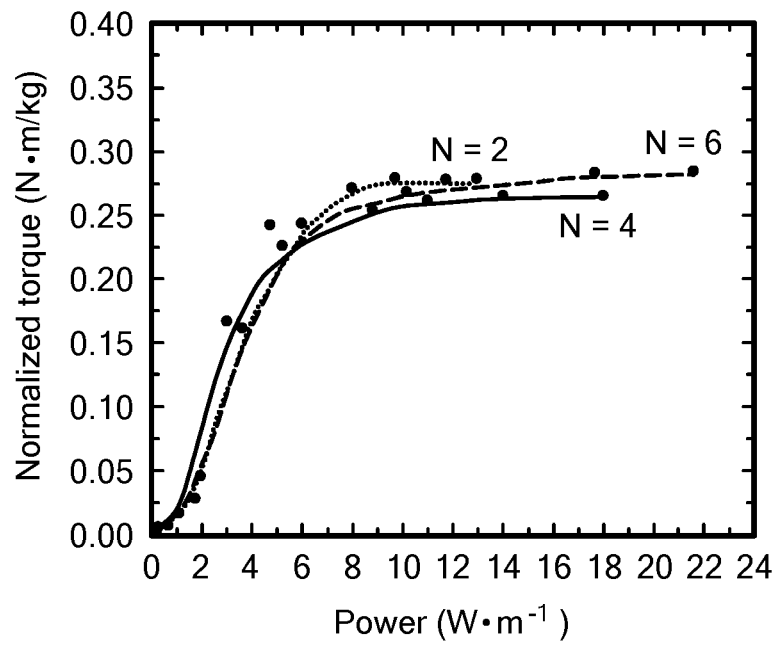
FIG. 4A depicts torque (normalized over the mass of the actuating section of the yarn and the inserted twist) as a function of input power (normalized over the length of the yarn) for yarns of N=2, 4 and 6 strands of SMA in accordance with embodiments of the present invention.

A gravimetric torque of 8-10 N·m/kg was achieved in the example described above. For comparison, this gravimetric toque exceeds that typical of a high-performance, ungeared, commercial, direct-drive electric motor. FIG. 4A illustrates the torque (normalized over the mass of the actuating section of the yarn and the inserted twist) as a function of the input power (normalized over the length of the yarn).

The specific work capacity can be estimated from the maximum torque and torsional stroke, according to $$W_m = \frac{1}{4}\tau_m \theta_m.$$

Figure 4B:
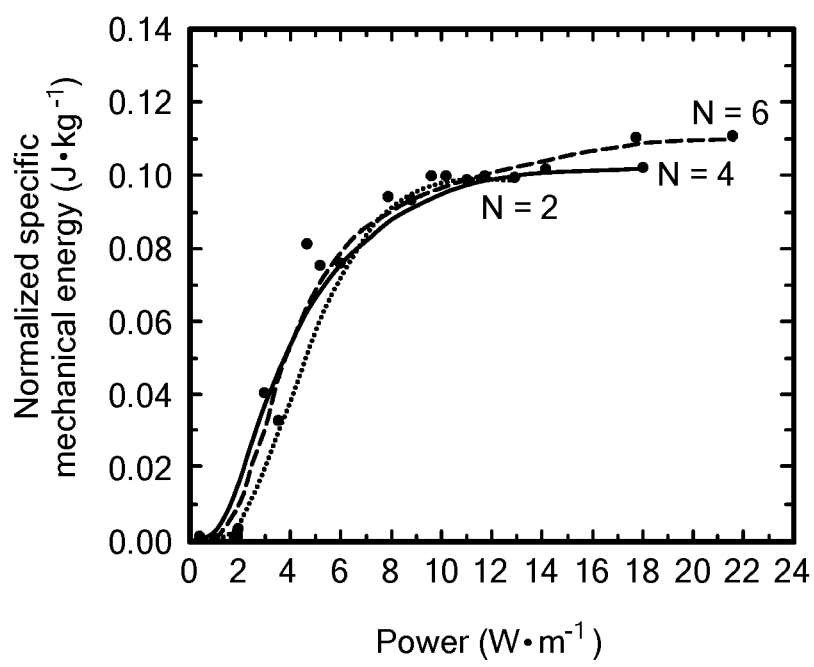
In FIG. 4B, the specific mechanical energy (normalized over the mass of the yarn and square of number of inserted twist) for twisted N-ply yarn is plotted as a function of the input power (normalized over the length of the yarn).
Figure 4C:
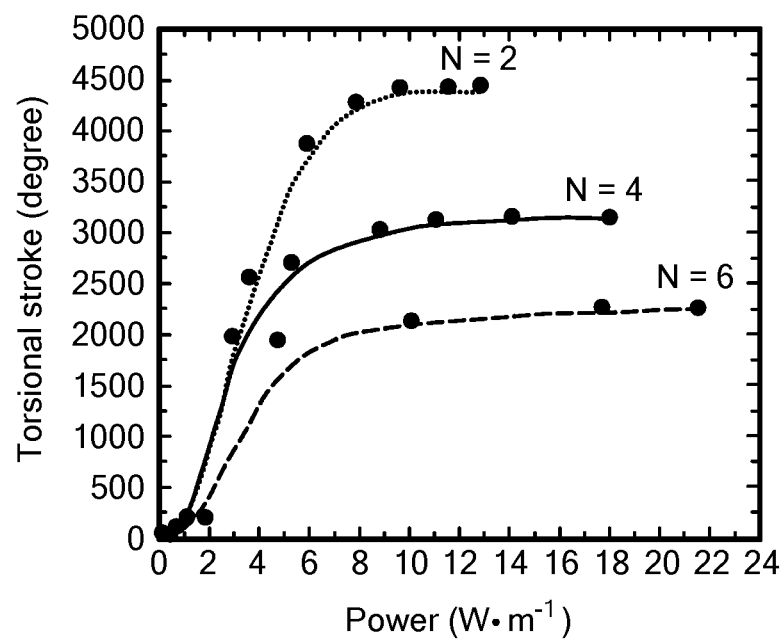
In FIG. 4C, the torsional stroke for twisted N-ply yarn is plotted as a function of the input power (normalized over the length of the yarn).

A specific work capacit of up to 170 kJ·m$^{-3}$ was measured for a yarn with two NiTi strands. Specific work capacity (normalized over the mass of the yarn and square of number of inserted twist) may be visualized as a function of input power with reference to FIGS. 4A-4B. More particularly, FIG. 4A depicts normalized torque as a function of input power for yarns of N=2, 4 and 6 strands of SMA. As the plot suggests, the normalized torque scales with the mass and the number of the inserted twist. In FIG. 4B, the specific mechanical energy is plotted for twisted N-ply yarn as a function of the input power.

Figure 5A:
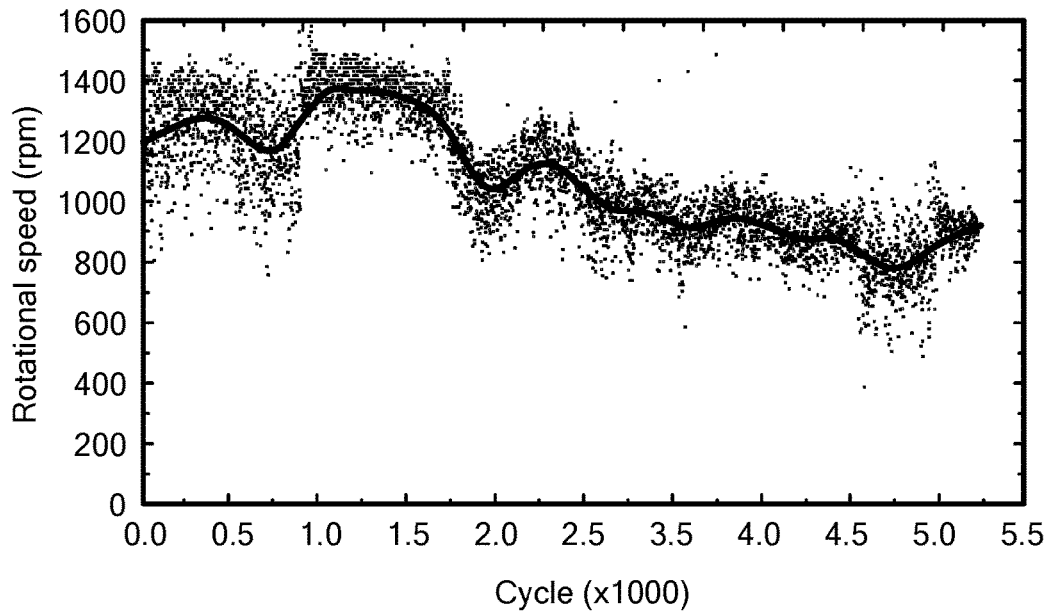
FIG. 5A shows a plot of rotational speed vs. number of actuations for a torsional actuator in accordance with an embodiment of the present invention.
Figure 5B:
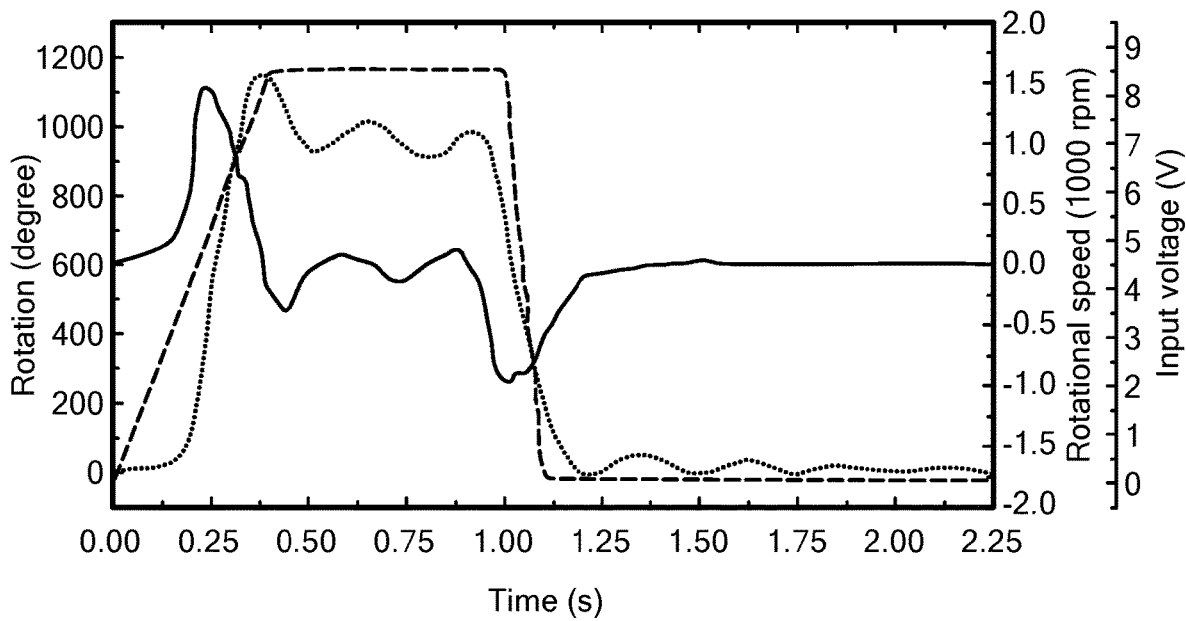
FIG. 5B shows wave shapes of an applied excitation and actuator response, in accordance with embodiments of the present invention.

Cycle life was measured for a proptotype of a NiTi twisted pair torsional artificial muscle with a length of 127 mm and twist of 394 turns/m. The muscle was under a load of 35 MPa. After 5,200 cycles, some deterioration in rotational speed, as indicated in the data plotted in FIG. 5A. To measure cycle life, an excitation ramp was applied with a 400 ms rise time, 600 ms peak time, and 100 ms fall time, as shown in FIG. 5B. With the square waves, the yarn broke in fewer than 3,200 cycles, while, under similar experimental conditions, ramping the voltage up and down extended the cycle life slightly.

Further explanation of operational mechanisms in accordance with embodiments of the present invention may be found in the following publications, both of which are incorporated herein by reference:

Mirvakili et al., "*Fast Torsional Artificial Muscles from NiTi Twisted Yarns,*" *ACS Appl. Mater. Interfaces*, vol. 9, pp. 16321-26 (Apr. 27, 2017); and Mirvakili et al., "*A torsional artificial muscle from twisted nitinol microwire,*" *Proc. SPIE* 10163, *Electroactive Polymer Actuators and Devices (EAPAD)*, 101630S (Apr. 17, 2017).

The embodiments of the invention described above are intended to be merely exemplary; numerous variations and modifications will be apparent to those skilled in the art. All such variations and modifications are intended to be within the scope of the present invention as defined in any appended claims.

We claim:

1. A torsional actuator comprising:
a yarn, having a first portion and a second portion along a length, comprising a homochirally twisted plurality of homogeneous strands of shape memory material; and
a controller for programmable heating of at least a portion of the yarn,
wherein each homogeneous strand of the first portion is coated with a coating material of higher electrical conductivity than an electrical conductivity of the shape memory material, and
wherein the second portion is configured to preferentially undergo a change in a physical property selected from the group consisting of length, amount of twist, and combinations thereof, relative to the first portion upon application of the programmable heating.

2. A torsional actuator in accordance with claim 1, wherein the programmable heating includes Joule heating.

3. A torsional actuator in accordance with claim 2, wherein the Joule heating includes electrical current flow traversing the length of the yarn.

4. A torsional actuator in accordance with claim 1, wherein the homochirally twisted plurality of homogeneous strands includes at least two strands of shape memory alloy.

5. A torsional actuator in accordance with claim 4, wherein the shape memory alloy includes an alloy comprising nickel and titanium.

6. A torsional actuator in accordance with claim 1, wherein the shape memory material is nitinol microwire.

* * * * *